(12) United States Patent
Al Hatib et al.

(10) Patent No.: US 11,317,820 B2
(45) Date of Patent: *May 3, 2022

(54) HEALTH MONITORING UNIT WITH HYPOTENSION PREDICTIVE GRAPHICAL USER INTERFACE (GUI)

(71) Applicant: Edwards Lifesciences Corporation, Irvine, CA (US)

(72) Inventors: Feras Al Hatib, Irvine, CA (US); Peter James Ifft, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1242 days.

This patent is subject to a terminal disclaimer.

(21) Appl. No.: 15/649,872

(22) Filed: Jul. 14, 2017

(65) Prior Publication Data

US 2018/0028076 A1 Feb. 1, 2018

Related U.S. Application Data

(60) Provisional application No. 62/366,953, filed on Jul. 26, 2016.

(51) Int. Cl.
*A61B 5/00* (2006.01)
*A61B 5/026* (2006.01)
(Continued)

(52) U.S. Cl.
CPC ............ *A61B 5/026* (2013.01); *A61B 5/7275* (2013.01); *A61B 5/7282* (2013.01); *A61B 5/742* (2013.01);
(Continued)

(58) Field of Classification Search
CPC ........ G16H 20/60; G16H 20/30; G16H 40/67; G16H 10/60; G16H 50/20; G16H 15/00;
(Continued)

(56) References Cited

U.S. PATENT DOCUMENTS

2005/0187796 A1 8/2005 Rosenfeld et al.
2008/0319332 A1 12/2008 Sommo et al.
(Continued)

FOREIGN PATENT DOCUMENTS

EP 2730302 A1 5/2014
KR 10-2009-0049709 A 5/2009
(Continued)

OTHER PUBLICATIONS

Int'l Search Report for PCT/US2017/042221, dated Sep. 21, 2017.
(Continued)

*Primary Examiner* — Reginald R Reyes (57) ABSTRACT

A health monitoring unit includes a hardware processor, a memory, a display, and a graphical user interface (GUI) stored in the memory. The GUI is executed by the processor to provide a selection screen enabling a user to select parameters for viewing on the display from among health parameters of a living subject being tracked by the health monitoring unit. The GUI also presents a main screen showing the parameters selected by the user, the main screen including an icon for communicating a hypotension probability index (HPI) status of the living subject. In addition, the GUI overlays an alarm screen as a pop-up on the display if the HPI of the living subject satisfies a predetermined risk criteria, and enables the user to access an HPI diagnostic screen showing values for a subset of the health parameters identified as predictive of a future hypotension event for the living subject.

27 Claims, 9 Drawing Sheets

(51) Int. Cl.
*G16H 40/63* (2018.01)
*G16H 50/30* (2018.01)
*G16H 40/40* (2018.01)
*A61B 8/06* (2006.01)

(52) U.S. Cl.
CPC ............ *A61B 5/746* (2013.01); *A61B 5/7435* (2013.01); *A61B 5/7475* (2013.01); *A61B 8/06* (2013.01); *A61B 8/065* (2013.01); *G16H 40/40* (2018.01); *G16H 40/63* (2018.01); *G16H 50/30* (2018.01)

(58) Field of Classification Search
CPC ........ G16H 20/10; G16H 20/70; G16H 50/70; G16H 70/40; G16H 20/17; G16H 40/63; G16H 50/30; G16H 70/20; G16H 80/00
See application file for complete search history.

(56) References Cited

U.S. PATENT DOCUMENTS

| | | | |
|---|---|---|---|
| 2011/0245631 A1 | 10/2011 | Genc | |
| 2013/0096402 A1* | 4/2013 | Olde | A61B 5/02416 600/324 |
| 2013/0262357 A1 | 10/2013 | Amarasingham et al. | |
| 2014/0107433 A1 | 4/2014 | Wegerich | |
| 2014/0364750 A1 | 12/2014 | Brumfield et al. | |
| 2015/0025329 A1 | 1/2015 | Amarasingham et al. | |
| 2015/0116333 A1 | 4/2015 | Harper et al. | |
| 2015/0164437 A1 | 6/2015 | McCombie et al. | |
| 2015/0282717 A1 | 10/2015 | McCombie et al. | |
| 2016/0012197 A1* | 1/2016 | Eromo | G06Q 10/10 705/2 |
| 2017/0116497 A1* | 4/2017 | Georgescu | G06K 9/2063 |
| 2020/0260965 A1* | 8/2020 | Munoz | G16H 50/30 |

FOREIGN PATENT DOCUMENTS

| | | |
|---|---|---|
| WO | 2004034898 A2 | 4/2004 |
| WO | 2015183689 A1 | 12/2015 |
| WO | 2016022989 A2 | 2/2016 |

OTHER PUBLICATIONS

Int'l. Search Report for PCT/US2017/039974, dated Aug. 28, 2017.
Int'l. Search Report for PCT/US2017/042879, dated Sep. 21, 2017.
Int'l. Search Report for PCT/US2017/042363, dated Oct. 20, 2017.
D. Hayn, A Biosignal Analysis Applied for Developing an Algorithm Predicting Critical Situations of High Risk Cardiac Patients by Hemodynamic Monitoring; Computers in Cardiology 2009; 36: 629-632.
F. Chiarugi, Predicting the Occurrence of Acute Hypotensive Episodes: The PhysioNet Challenge; Computers in Cardiology 2009; 36:621-624.
F. Jousset, Computers in Cardiology/Physionet Challenge 2009: Predicting Acute Hypotensive Episodes, 2009; 36:637-640.
GB Moody et al.; Predicting Acute Hypotensive Episodes: The 10th Annual PhysioNet/Computers in Cardiology Challenge, 2009; 36:541-544.
JH Henriques et al., Prediction of Acute Hypotensive Episodes Using Neural Network Multi-models; Computers in Cardiology 2009; 36-549-552.
K Jin et al., Smooting and Discriminating MAP Data; Computers in Cardiology 2009; 36: 633-636.
MA Mneimneh et al., A Rule-Based Approach for the Prediction of Acute Hypotensive Episodes; Computers in Cardiology 2009; 36:557-560.
P Langley, et al., Predicting Acute Hypotensive Episodes From Mean Arterial Pressure; Computers in Cardiology 2009; 36: 553-556.
PA Fournier et al., Acute Hypotension Episode Prediction Using Information Divergence for a Feature Selection, and Non-Parametric Methods for Classification; Computers in Cardiology 2009; 36:625-628.
TCT Ho et al., Utilizing Histogram to Identify Patients Using Pressors for Acute Hypotension, Computers in Cardiology 2009; 36:797-800.
X Chen et al., Forecasting Acute Hypotensive Episodes in Intensive Care Patients Based on a Peripheral Arterial Blood Pressure Waveform, Computers in Cardiology 2009; 36:545-548.

* cited by examiner

_(10)_ Patent No.: US 11,317,820 B2

HEALTH MONITORING UNIT WITH HYPOTENSION PREDICTIVE GRAPHICAL USER INTERFACE (GUI)

BACKGROUND

Hypotension, or low blood pressure, can be a harbinger of serious medical complications, and even mortality, for patients undergoing surgery and those acutely or critically ill patients receiving treatment in an intensive care unit (ICU). The dangers associated with the occurrence of hypotension in a patient are due both to the potential injury caused by the hypotension itself and to the many serious underlying medical disorders that the occurrence of hypotension may signify.

In and of itself, hypotension in surgical patients or critically ill patients is a serious medical condition. For example, in the operating room (OR) setting, hypotension during surgery is associated with increased mortality and organ injury. Even short durations of extreme hypotension during surgery are associated with acute kidney injury and myocardial injury. Among critically ill patients, in-hospital mortality may be nearly doubled for patients experiencing hypotension after emergency intubation. For surgical patients and seriously ill patients alike, hypotension, if not corrected, can impair organ perfusion, resulting in irreversible ischemic damage, neurological deficit, cardiomyopathy, and renal impairment.

In addition to posing serious risks to surgical patients and critically ill patients in its own right, hypotension can be a symptom of one or more other serious underlying medical conditions. Examples of underlying conditions for which hypotension may serve as an acute symptom include sepsis, myocardial infarction, cardiac arrhythmia, pulmonary embolism, hemorrhage, dehydration, anaphylaxis, acute reaction to medication, hypovolemia, insufficient cardiac output, and vasodilatory shock. Due to its association with such a variety of serious medical conditions, hypotension is relatively common, and is often seen as one of the first signs of patient deterioration in the OR and ICU. For instance, hypotension is seen in up to approximately thirty-three percent of surgeries overall, and up to eighty-five percent in high risk surgeries. Among ICU patients, hypotension occurs in from approximately twenty-four percent to approximately eighty-five percent of all patients, with the eighty-five percent occurrence being seen among critically ill patients.

Conventional patient monitoring for hypotension in the OR and ICU settings can include continuous or periodic blood pressure measurement. However, such monitoring, whether continuous or periodic, typically provides no more than a real-time assessment. As a result, hypotension in a surgical patient or critically ill patient is usually detected only after it begins to occur, so that remedial measures and interventions cannot be initiated until the patient has entered a hypotensive state. Although, as noted above, extreme hypotension can have potentially devastating medical consequences quite quickly, even relatively mild levels of hypotension can herald or precipitate cardiac arrest in patients with limited cardiac reserve.

In view of the frequency with which hypotension is observed to occur in the OR and ICU settings, and due to the serious and sometimes immediate medical consequences that can result when it does occurs, a solution enabling prediction of a future hypotension event, before its occurrence, is highly desirable.

SUMMARY

There are provided exemplary implementations of a health monitoring unit with a hypotension predictive graphical user interface (GUI), and methods for use by such a health monitoring unit, substantially as shown in and/or described in connection with at least one of the figures, and as set forth more completely in the claims.

DETAILED DESCRIPTION

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

The present application discloses a health monitoring unit with a hypotension predictive graphical user interface (GUI). The health monitoring unit converts data received from a hemodynamic sensor to digital hemodynamic data of a living subject and obtains health parameters that are often highly predictive of future hypotension for the living subject from the digital hemodynamic data. The health monitoring unit utilizes some or all of the health parameters to determine a risk score or hypotension probability index (hereinafter "HPI") corresponding to the probability of a future hypotension event for the living subject.

The hypotension predictive GUI of the health monitoring unit provides a health care worker such as a doctor or nurse (hereinafter "user") with powerful options for monitoring and evaluating the probability of a future hypotension event for the living subject. By providing a selection screen on a display of the health monitoring unit, the hypotension predictive GUI disclosed by the present application enables the user to select parameters for viewing on the display from among the health parameters of the living subject being tracked by the health monitoring unit. By presenting a main screen on the display that includes an icon for communicating the HPI status of the living subject regardless of the parameters selected by the user, the hypotension predictive GUI disclosed by the present application renders the HPI status of the living subject continuously observable by the user.

In addition, by overlaying an alarm screen as a pop-up on the health monitoring unit display if the HPI of the living subject satisfies a predetermined risk criteria, the hypotension predictive GUI disclosed by the present application ensures that a timely warning of a future hypotension event is provided to the user. Moreover, by enabling the user to access an HPI diagnostic screen showing values for a subset of the health parameters identified as predictive of the future hypotension event, the hypotension predictive GUI disclosed by the present application provides detailed diagnostic information allowing the user to identify a most probable cause of the future hypotension event as well as possible medical interventions for its prevention.

Figure 1:
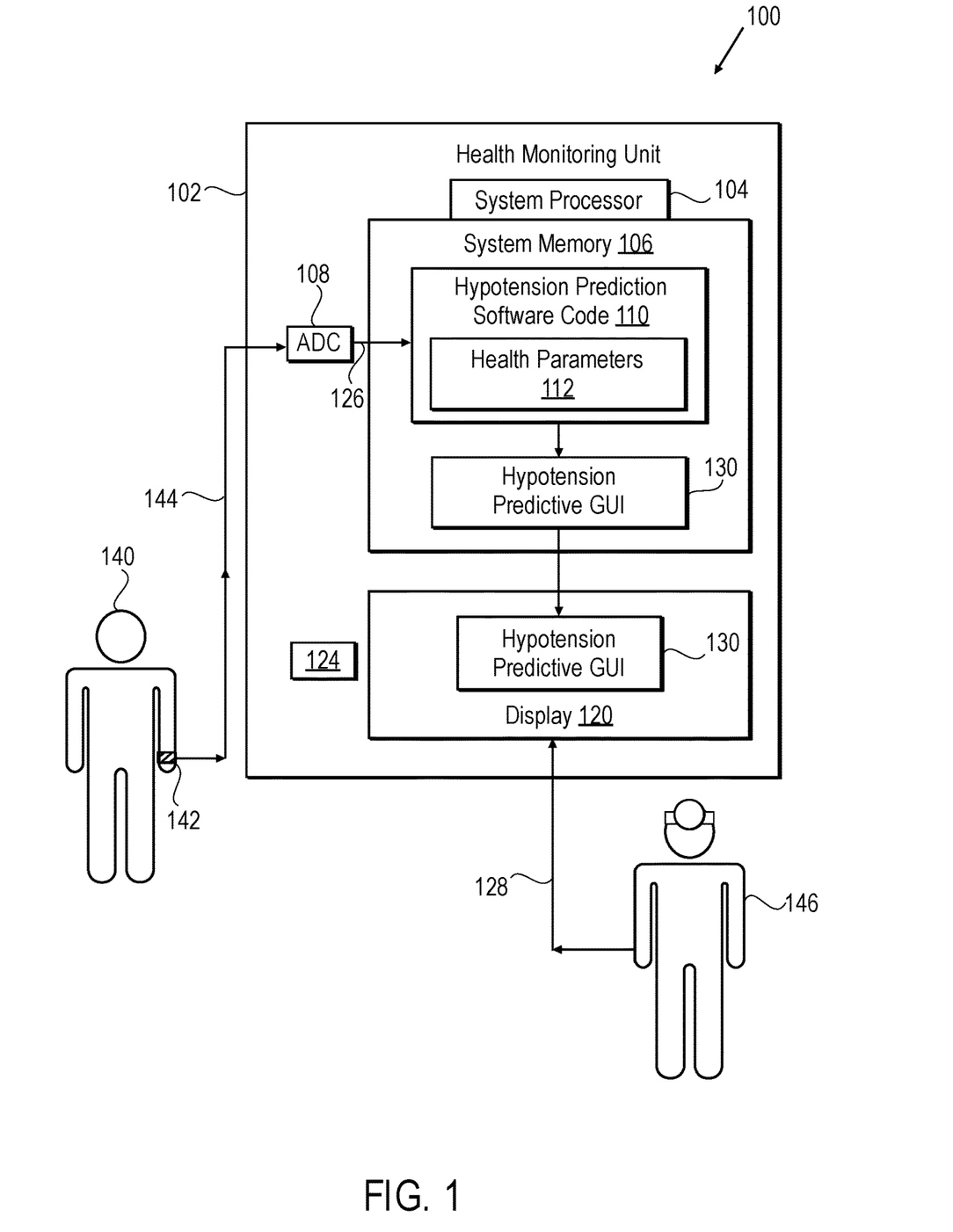
FIG. 1 shows a diagram of an exemplary health monitoring unit with a hypotension predictive graphical user interface (GUI), according to one implementation.

FIG. 1 shows a diagram of an exemplary system for performing health monitoring. System 100 includes health monitoring unit 102, which may be an integrated health monitoring unit, for example, and hemodynamic sensor 142 coupled to health monitoring unit 102. As shown in FIG. 1, health monitoring unit 102 includes system processor 104, implemented as a hardware processor, system memory 106, analog-to-digital converter (ADC) 108, display 120, and sensory alarm 124. As further shown in FIG. 1, system memory 106 of health monitoring unit 102 stores hypotension predictive GUI 130 and hypotension prediction software code 110 including health parameters 112.

It is noted that hypotension predictive GUI 130 is shown in FIG. 1 as being provided on display 120, as well as being stored in system memory 106 to indicate that hypotension predictive GUI 130 is executed by hardware processor 104 to provide an interactive user interface via display 120 of health monitoring unit 102. Also shown in FIG. 1 is digital hemodynamic data 126 generated by ADC 108 from signal 144 received from hemodynamic sensor 142.

Health monitoring unit 102 may be implemented within a patient care environment such as an intensive care unit (ICU) or operating room (OR), for example. As shown in FIG. 1, in addition to health monitoring unit 102 and hemodynamic sensor 142, the patient care environment includes patient 140 (hereinafter "living subject 140"), and healthcare worker 146 (hereinafter "user 146") trained to utilize health monitoring unit 102. As will be discussed in greater detail below, hypotension predictive GUI 130 is configured to receive inputs 128 from user 146, and to invoke sensory alarm 124 if the HPI for living subject 140 satisfies a predetermined risk criteria.

Hemodynamic sensor 142 is shown in an exemplary implementation in FIG. 1, and is attached to living subject 140. It is noted that hemodynamic sensor 142 may be a non-invasive or minimally invasive sensor attached to living subject 140. In one implementation, as represented in FIG. 1, hemodynamic sensor 142 may be attached non-invasively at an extremity of living subject 140, such as a wrist or finger of living subject 140. Although not explicitly shown in FIG. 1, in other implementations, hemodynamic sensor 142 may be attached non-invasively at an ankle or toe of living subject 140. Signal 144 received by health monitoring unit 102 from hemodynamic sensor 142 may include signals corresponding to the arterial pressure of living subject 140. Health monitoring unit 102 and hemodynamic sensor 142 may be configured such that signal 144 may be received by health monitoring unit 102 wirelessly, or via a wired connection with hemodynamic sensor 142.

According to the exemplary implementation shown in FIG. 1, system processor 104 is configured to utilize ADC 108 to convert signal 144 to digital hemodynamic data 126. System processor 104 is further configured to execute hypotension prediction software code 110 to transform digital hemodynamic data 126 to health parameters 112. System processor 104 is further configured to execute hypotension prediction software code 110 to determine the HPI for living subject 140 based on health parameters 112. In addition, system processor 104 is configured to execute hypotension predictive GUI 130 to invoke sensory alarm 124 if the HPI satisfies a predetermined risk criteria.

For example, system processor 104 may be configured to execute hypotension predictive GUI 130 to overlay an alarm screen as a pop-up on display 120 if the HPI of living subject 140 satisfies a predetermined risk criteria. In such an implementation, overlaying the alarm screen as a pop-up on display 120 may cause sensory alarm 124 to be invoked. Thus, hypotension predictive GUI 130 and/or sensory alarm 124 may be used by health monitoring unit 102 to warn of a hypotension event for living subject 140 predicted to occur approximately one to five minutes in the future, or up to approximately thirty minutes in the future.

In various implementations, sensory alarm 124 may be implemented as one or more of a visual alarm, an audible alarm, and a haptic alarm. For example, when implemented to provide a visual alarm, sensory alarm 124 may be invoked as flashing and/or colored graphics shown by hypotension predictive GUI 130 on display 120, and/or may include displaying the HPI via hypotension predictive GUI 130 on display 120. When implemented to provide an audible alarm, sensory alarm 124 may be invoked as any suitable warning sound, such as a siren or repeated tone. Moreover, when implemented to provide a haptic alarm, sensory alarm 124 may cause health monitoring unit 102 to vibrate or otherwise deliver a physical impulse perceptible to user 146.

It is noted that the HPI for living subject 140 is determined based on health parameters 112, which in turn are derived from signal 144 of living subject 140 received from hemodynamic sensor 142. Consequently, according to the inventive concepts disclosed by the present application, system processor 104 of health monitoring unit 102 is configured to execute hypotension prediction software code 110 to determine the HPI for living subject 140 without comparison with data corresponding to hypotension in other living subjects. In other words, hypotension prediction software code 110 determines the HPI for living subject 140 based on health parameters 112, without reference to a hypotension patient database storing information regarding hypotension in patients other than living subject 140.

Figure 2A:
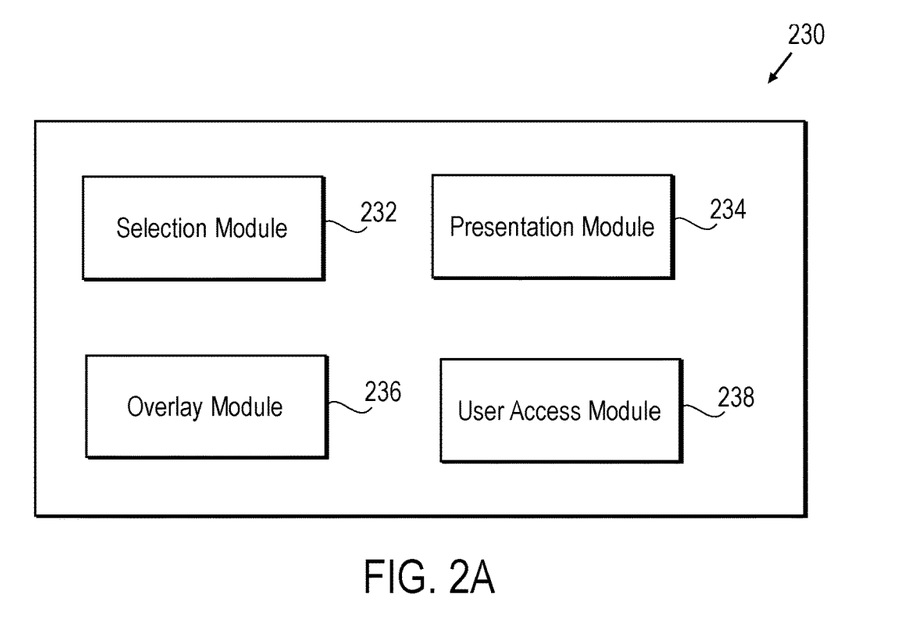
FIG. 2A shows a more detailed exemplary implementation of the hypotension predictive GUI shown in FIG. 1.

Referring to FIG. 2A, FIG. 2A shows a more detailed exemplary implementation of hypotension predictive GUI 130, in FIG. 1. In other words, hypotension predictive GUI 230, in FIG. 2A corresponds in general to hypotension predictive GUI 130, in FIG. 1, and each of hypotension predictive GUI 130 and hypotension predictive GUI 230 may share any of the characteristics attributed to either of hypotension predictive GUI 130 and hypotension predictive GUI 230 in the present application.

As shown in FIG. 2A, hypotension predictive GUI 230 includes several modules for facilitating interaction by a user, such as user 146, in FIG. 1, with hypotension predictive GUI 230. Among the modules included in hypotension predictive GUI 230 are selection module 232, presentation module 234, overlay module 236, and user access module 238. It is noted that the functionality of selection module 232, presentation module 234, overlay module 236, and user access module 238 will be described below with reference to flowchart 360, in FIG. 3.

Figure 2B:
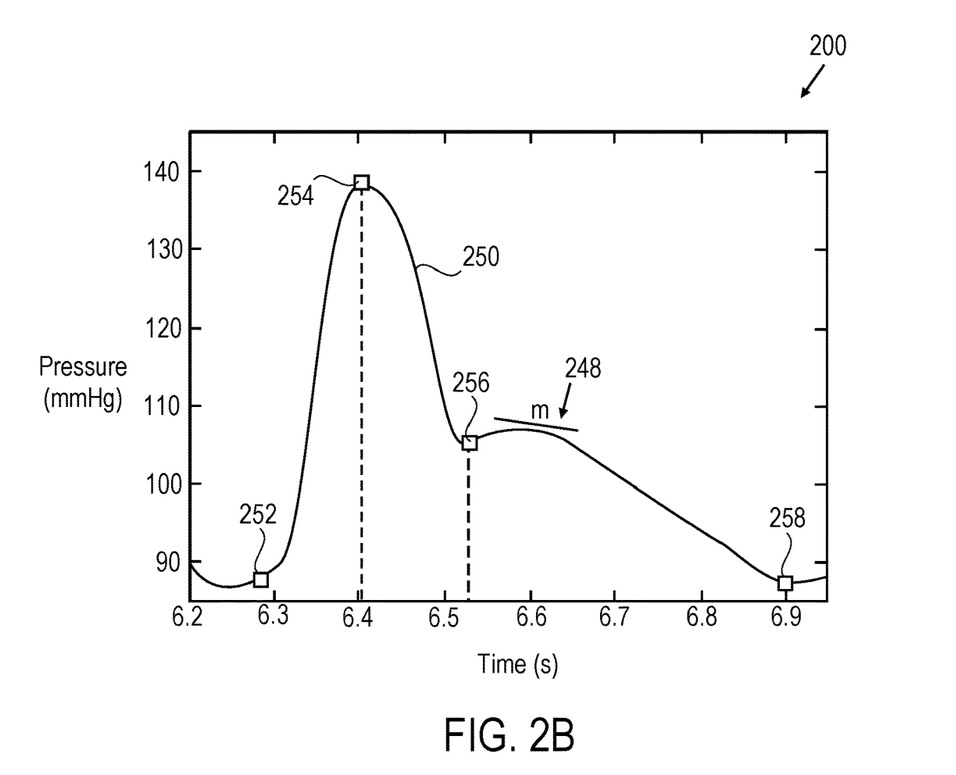
FIG. 2B shows a trace of an arterial pressure waveform including exemplary indicia corresponding to the probability of future hypotension in a living subject.

Continuing to FIG. 2B, diagram 200 in FIG. 2B shows a trace of arterial pressure waveform 250 including exemplary indicia for determining the HPI for living subject 140. Arterial pressure waveform 250, which may be a central arterial pressure waveform of living subject 140, for example, may correspond to digital hemodynamic data 126, converted by ADC 108 of health monitoring unit 102 from signal 144 received from hemodynamic sensor 142.

As shown in FIG. 2B, arterial pressure waveform 250 includes exemplary indicia 252, 254, 256, and 258, corresponding respectively to the start of a heartbeat, the maximum systolic pressure marking the end of systolic rise, the presence of the dicrotic notch marking the end of systolic decay, and the diastole of the heartbeat of living subject 140. Also shown by diagram 200 is exemplary slope 248 of arterial pressure waveform 250. The indicia extracted from arterial pressure waveform 250, such as exemplary slope 248 and exemplary indicia 252, 254, 256, and 258, may be transformed by hypotension prediction software code 110 to health parameters 112.

In addition to the indicia 252, 254, 256, and 258 of arterial pressure waveform 250 per se, the behavior of arterial pressure waveform 250 during the intervals between those indicia may also be used as indicia for determining the HPI for living subject 140. For example, the interval between the start of the heartbeat at indicia 252 and the maximum systolic pressure at indicia 254 marks the duration of the systolic rise (hereinafter "systolic rise 252-254"). The systolic decay of arterial pressure waveform 250 is marked by the interval between the maximum systolic pressure at indicia 254 and the dicrotic notch at indicia 256 (hereinafter "systolic decay 254-256"). Together, systolic rise 252-254 and systolic decay 254-256 mark the entire systolic phase (hereinafter "systolic phase 252-256"), while the interval between the dicrotic notch at indicia 256 and the diastole at indicia 258 mark the diastolic phase of arterial pressure waveform 250 (hereinafter "diastolic phase 256-258").

Also of potential diagnostic interest is the behavior of arterial pressure waveform 250 in the interval from the maximum systolic pressure at indicia 254 to the diastole at indicia 258 (hereinafter "interval 254-258"), as well as the behavior of arterial pressure waveform 250 from the start of the heartbeat at indicia 252 to the diastole at indicia 258 (hereinafter "heartbeat interval 252-258"). The behavior of arterial pressure waveform 250 during intervals: 1) systolic rise 252-254, 2) systolic decay 254-256, 3) systolic phase 252-256, 4) diastolic phase 256-258, 5) interval 254-258, and 6) heartbeat interval 252-258 may be determined by measuring the area under the curve of arterial pressure waveform 250 and the standard deviation of arterial pressure waveform 250 in each of those intervals, for example. The respective areas and standard deviations measured for intervals 1, 2, 3, 4, 5, and 6 above may serve as additional indicia for determining the HPI for living subject 140.

Figure 3:
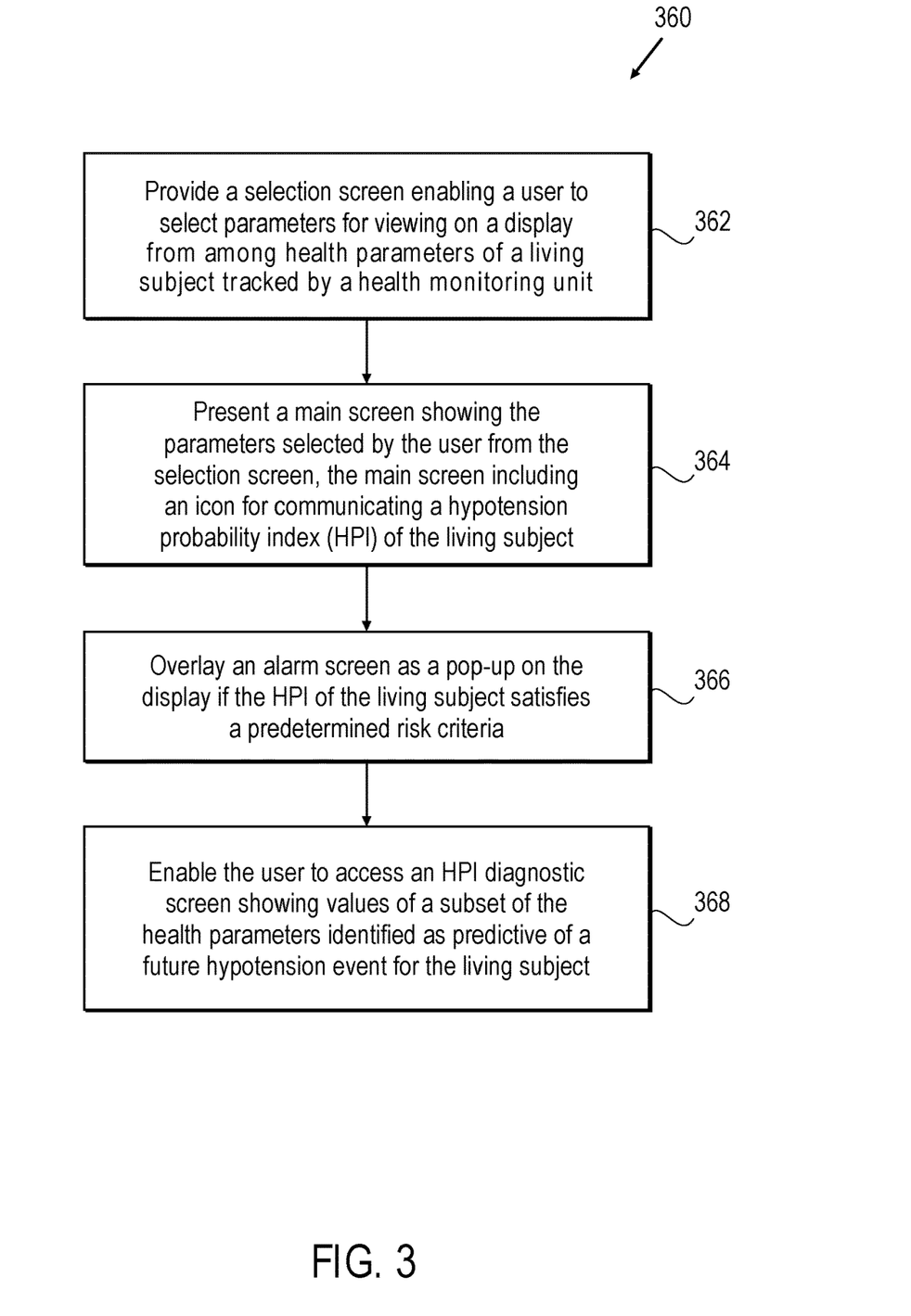
FIG. 3 is a flowchart presenting an exemplary method for use by a health monitoring unit with a hypotension predictive GUI.

Example implementations of the present inventive concepts will be further described below with reference to FIG. 3, FIGS. 4A, 4B, 4C, and 4D (hereinafter "FIGS. 4A-4D"), and FIGS. 5A and 5B. FIG. 3 presents flowchart 360 outlining an exemplary method for use by health monitoring unit 102 including hypotension predictive GUI 130/230. FIGS. 4A-4D show user interaction screens provided by hypotension predictive GUI 130/230, executed by system processor 104, through use of respective selection module 232, presentation module 234, overlay module 236, and user access module 238, according to one implementation. FIGS. 5A and 5B show user interaction screens provided by hypotension predictive GUI 130/230, executed by system processor 104, through use of respective selection module 232, presentation module 234, overlay module 236, and user access module 238, according to another implementation.

It is noted that the various user interaction screens shown by FIGS. 4A-4D are depicted as being provided by hypotension predictive GUI 430 via display 420, while the user interaction screens shown by FIGS. 5A and 5B are depicted as being provided by hypotension predictive GUI 530 via display 520. Hypotension predictive GUI 430/530, in FIGS. 4A-4D, 5A, and 5B corresponds in general to hypotension predictive GUI 130/230, in FIG. 1/2B. That is to say, each of hypotension predictive GUI 130/230/430/530 may share any of the characteristics attributed to any other hypotension predictive GUI 130/230/430/530 in the present application.

In addition, display 420/520, in FIGS. 4A-4D, 5A, and 5B corresponds in general to display 120, in FIG. 1. Thus, each of display 120/420/520 may share any of the characteristics attributed to any other display 120/420/520 in the present application. Display 120/420/520 may take the form of a liquid crystal display (LCD), a light-emitting diode (LED) display, an organic light-emitting diode (OLED) display, or another suitable display screen that performs a physical transformation of signals to light.

Referring to FIGS. 1, 2A, 3, and 4A in combination, flowchart 360 begins with providing selection screen 462 enabling user 146 to select parameters 472 and 484 for viewing on display 120/420 from among health parameters 112/412 of living subject 140 being tracked by health monitoring unit 102 (action 362). Selection screen 462 is provided on display 120/420 of health monitoring unit 102 by hypotension predictive GUI 130/230/430, executed by system processor 104, and through use of selection module 232.

Figure 4A:
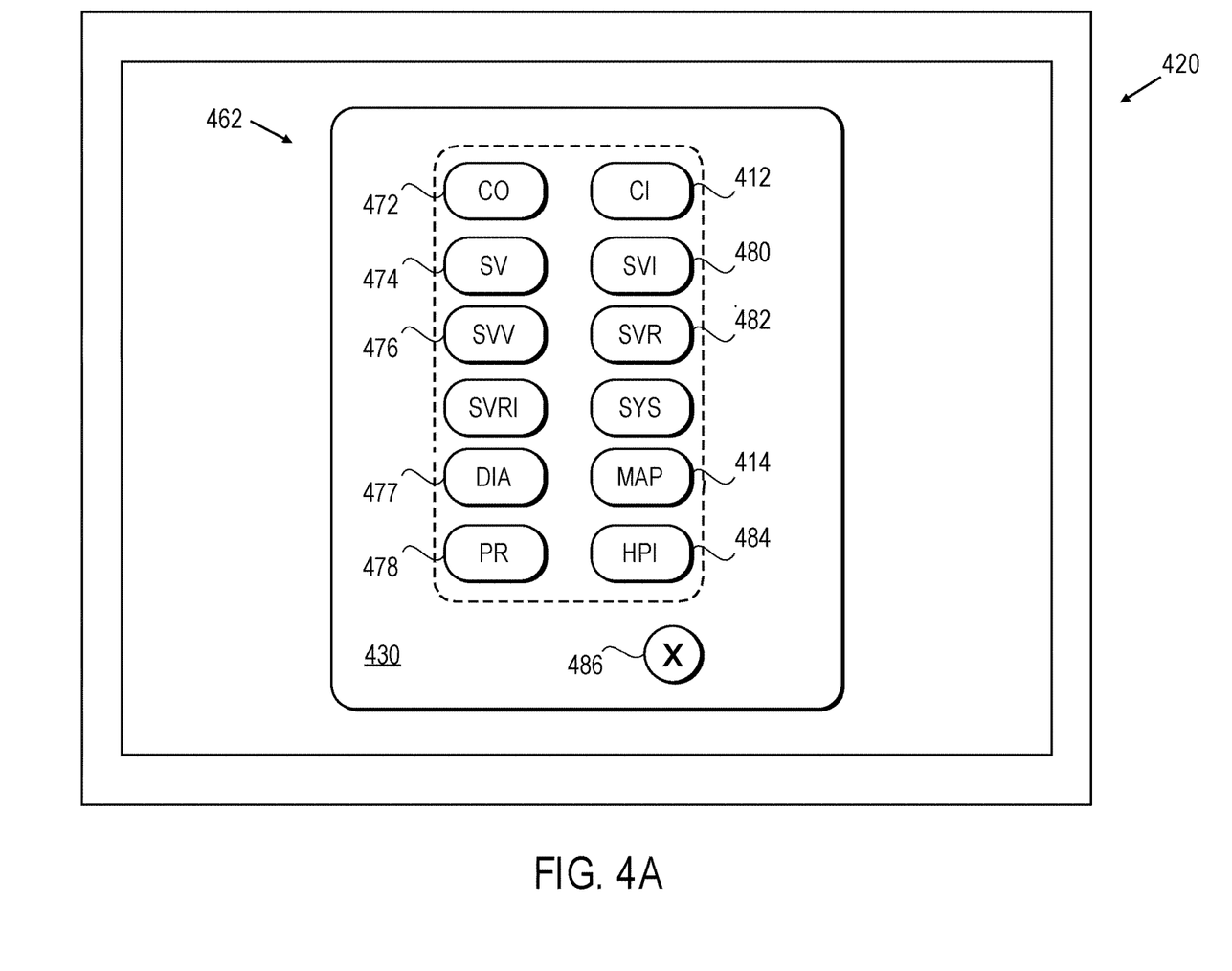
FIG. 4A shows an exemplary selection screen of a hypotension predictive GUI provided on a display of a health monitoring unit, according to one implementation.
Figure 5A:
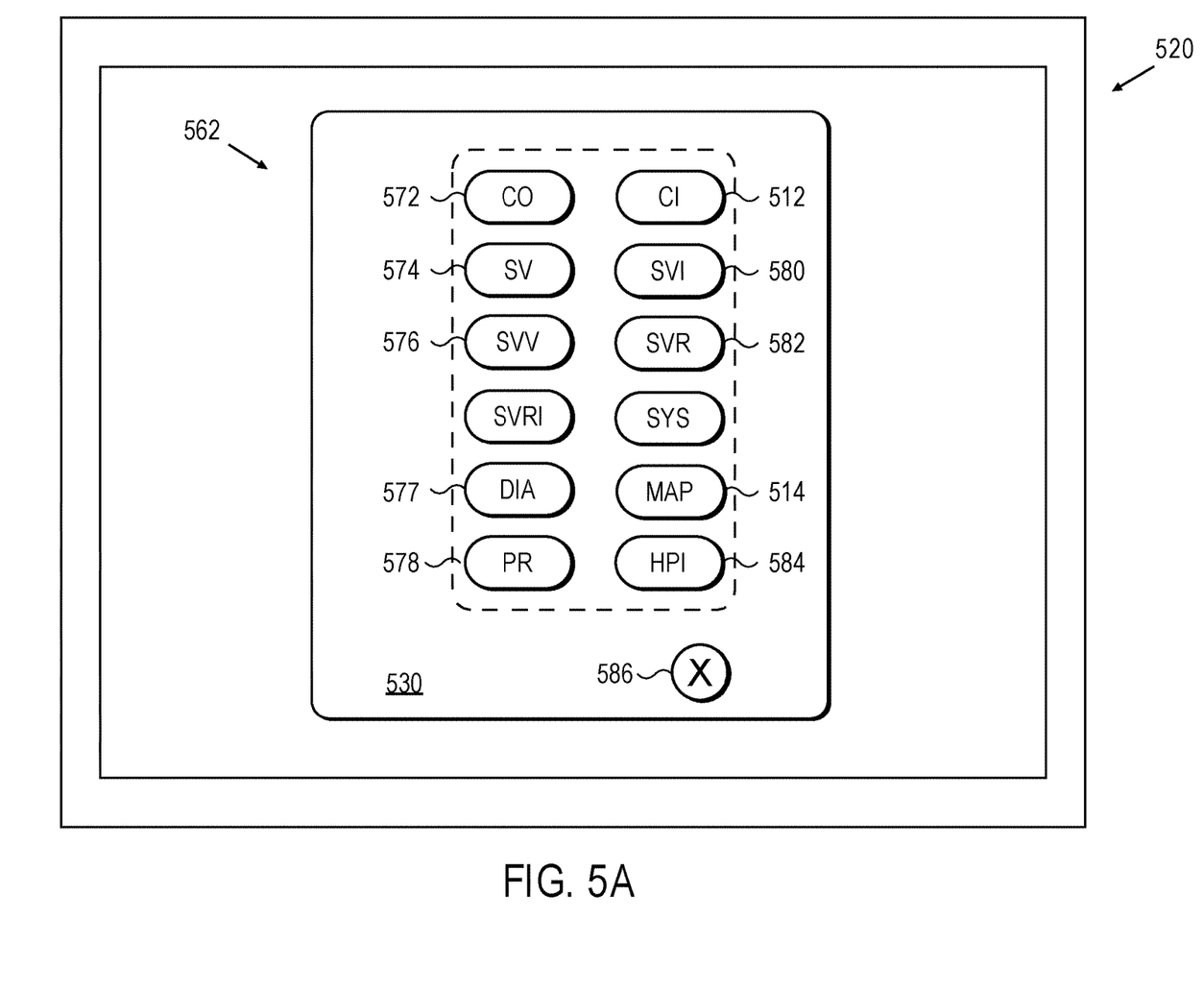
FIG. 5A shows an exemplary selection screen of a hypotension predictive GUI provided on a display of a health monitoring unit, according to another implementation.
Figure 5B:
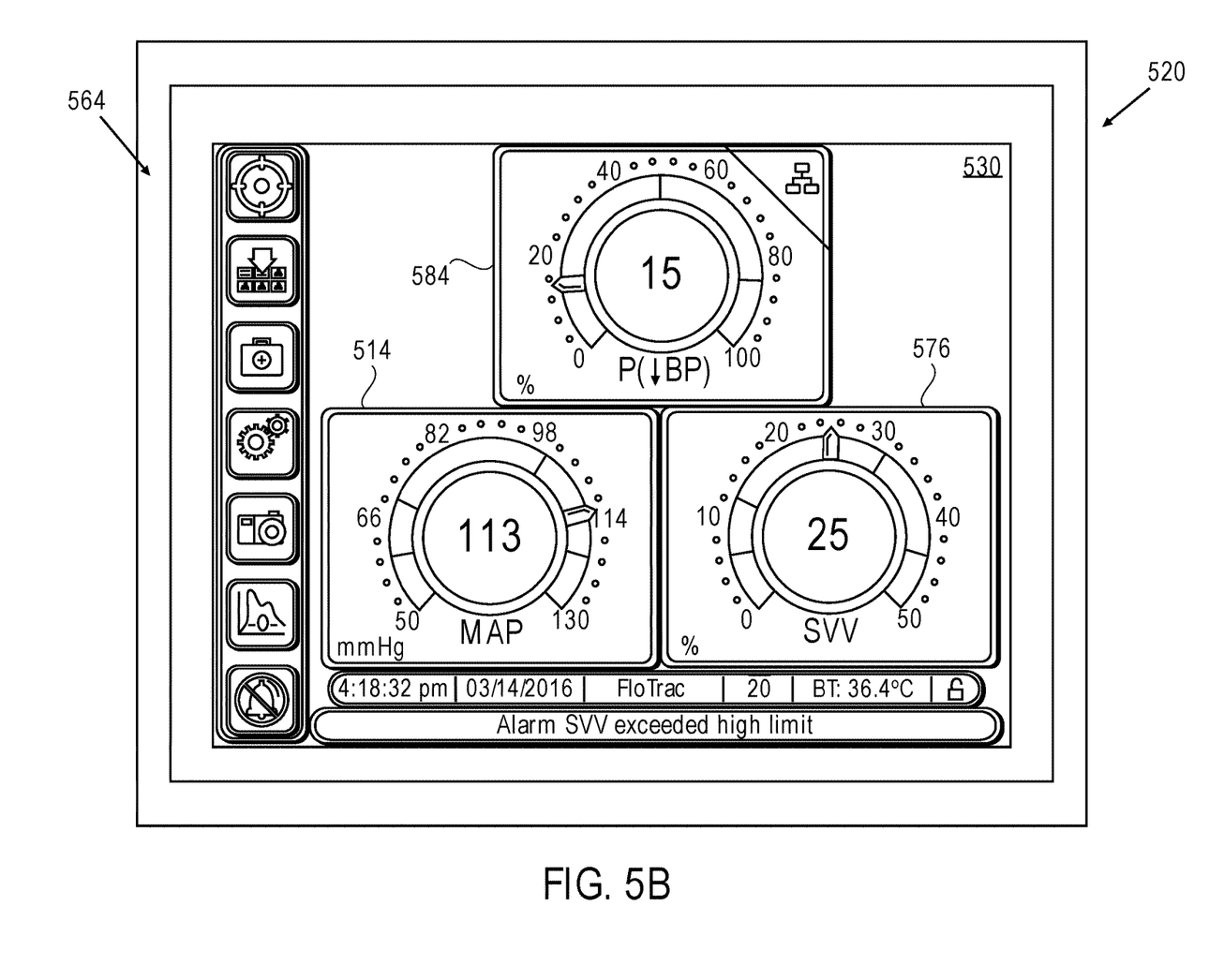
FIG. 5B shows an exemplary main screen of a hypotension predictive GUI presented on a display of a health monitoring unit, according to another implementation.

As shown by FIG. 4A, selection screen 462 of hypotension predictive GUI 130/230/430 enables user 146 to select from among health parameters 112/412 including cardiac output (CO) 472, stroke volume (SV) 474, stroke volume variation (SVV) 476, diastolic pressure (DIA) 477, pulse rate (PR) 478, stroke volume index (SVI) 480, systemic vascular resistance (SVR) 482, mean arterial pressure (MAP) 414, and HPI 484. In addition, health parameters 112/412 being tracked by health monitoring unit 102 include systemic vascular resistance index (SVRI), cardiac index (CI), and systolic pressure (SYS). It is noted that health parameters 112/412 being tracked by health monitoring unit 102 may further include additional parameters not represented on selection screen 462. Also shown in FIG. 4A is exit button 486 enabling user 146 to close selection screen 462 of hypotension predictive GUI 130/230/430.

According to the exemplary implementation shown by FIG. 4A, hypotension predictive GUI 130/230/430 is implemented as a touch screen user interface. However, in other implementations, hypotension predictive GUI 130/230/430 may be configured to receive inputs 128 from user 146 via a keyboard, via another type of input device, such as a mouse or pressure pad, or as voice commands spoken by user 146, for example.

As shown by the shadowing of parameters 476, 480, and 484, user 146 has selected CO 472 and HPI 484 for viewing on display 120/420 of health monitoring unit 102 from among health parameters 112/412 being tracked by health monitoring unit 102.

Figure 4B:
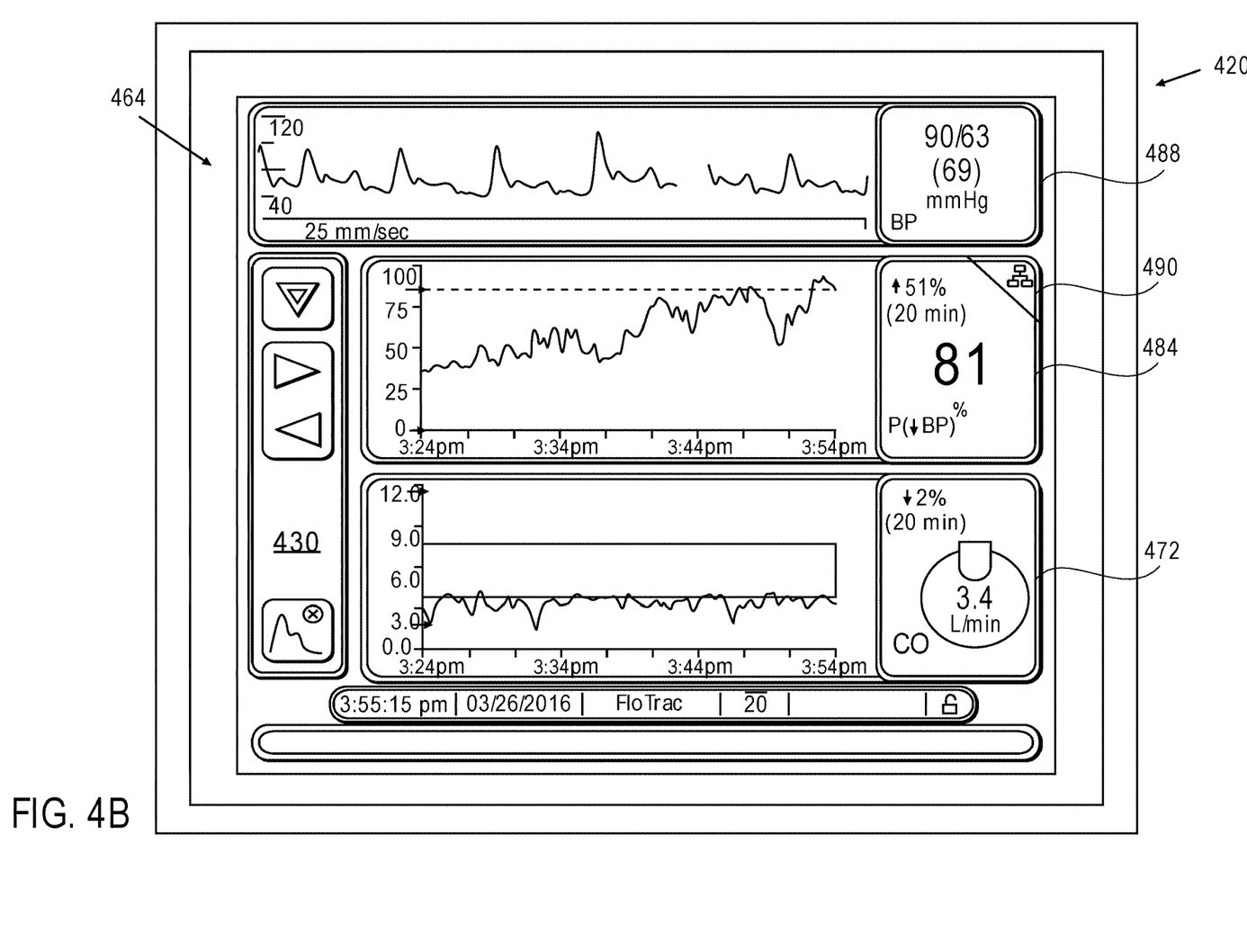
FIG. 4B shows an exemplary main screen of a hypotension predictive GUI presented on a display of a health monitoring unit, according to one implementation.

Referring to FIG. 4B in combination with FIGS. 1, 2A, and 3, flowchart 360 continues with presenting main screen 464 of hypotension predictive GUI 130/230/430 showing parameters CO 472 and HPI 484 selected by user 146 from selection screen 462 (action 364). It is noted that HPI 484 is depicted visually on interactive screens of hypotension predictive GUI 130/230/330 other than selection screen 462 as "P($\downarrow$BP)" and is shown on main screen 464 as P($\downarrow$BP) 484. It is further noted that the acronym HPI and its symbolic representation as P($\downarrow$BP) may be used interchangeably hereinafter. Main screen 464 is provided on display 120/420 of health monitoring unit 102 by hypotension predictive GUI 130/230/430, executed by system processor 104, and through use of presentation module 234.

As shown by FIG. 4B, main screen 464 of hypotension predictive GUI 130/230/430 shows P($\downarrow$BP) 484 numerically and as a trace displayed as a function of time. The trace as a function of time and numerical value shown for each of CO 472 and P($\downarrow$BP) 484, as well as for blood pressure (BP) 488, which may be included as a default parameter from among health parameters 112/412, may be shown continuously on main screen 464, and may be updated periodically, such as every approximately twenty seconds, for example.

According to the implementation shown by FIG. 4B, P($\downarrow$BP) 484 is shown as a number between zero and one hundred (0-100) corresponding to the probability that living subject 140 will experience a hypotension event. That is to say, a P($\downarrow$BP) near zero indicates that a hypotension event is highly unlikely, while a P($\downarrow$BP) near 100 indicates a high probability of an impending hypotension event. The trace and numerical value of P($\downarrow$BP) 484 may exhibit a color corresponding in general to the probability of a future hypotension event for living subject 140. For example, a relatively low P($\downarrow$BP), such as a P($\downarrow$BP) of less than or equal to 50 may cause the trace and/or numerical value of P($\downarrow$BP) 484 to appear green on main screen 464. However, a higher P($\downarrow$BP), such as a P($\downarrow$BP) between 50 and 85, for example, may cause the trace and/or numerical value of P($\downarrow$BP) 484 to appear yellow, while a high P($\downarrow$BP), such as a P($\downarrow$BP) over 85, may cause the trace and/or numerical value of P($\downarrow$BP) 484 to turn red.

In addition to the features described above, main screen 464 of hypotension predictive GUI 130/230/430 provides shortcut button 490 enabling user 146 direct access to an HPI diagnostic screen, described below, including additional data for evaluating the probability and likely cause of a future hypotension event for living subject 140.

Figure 4C:
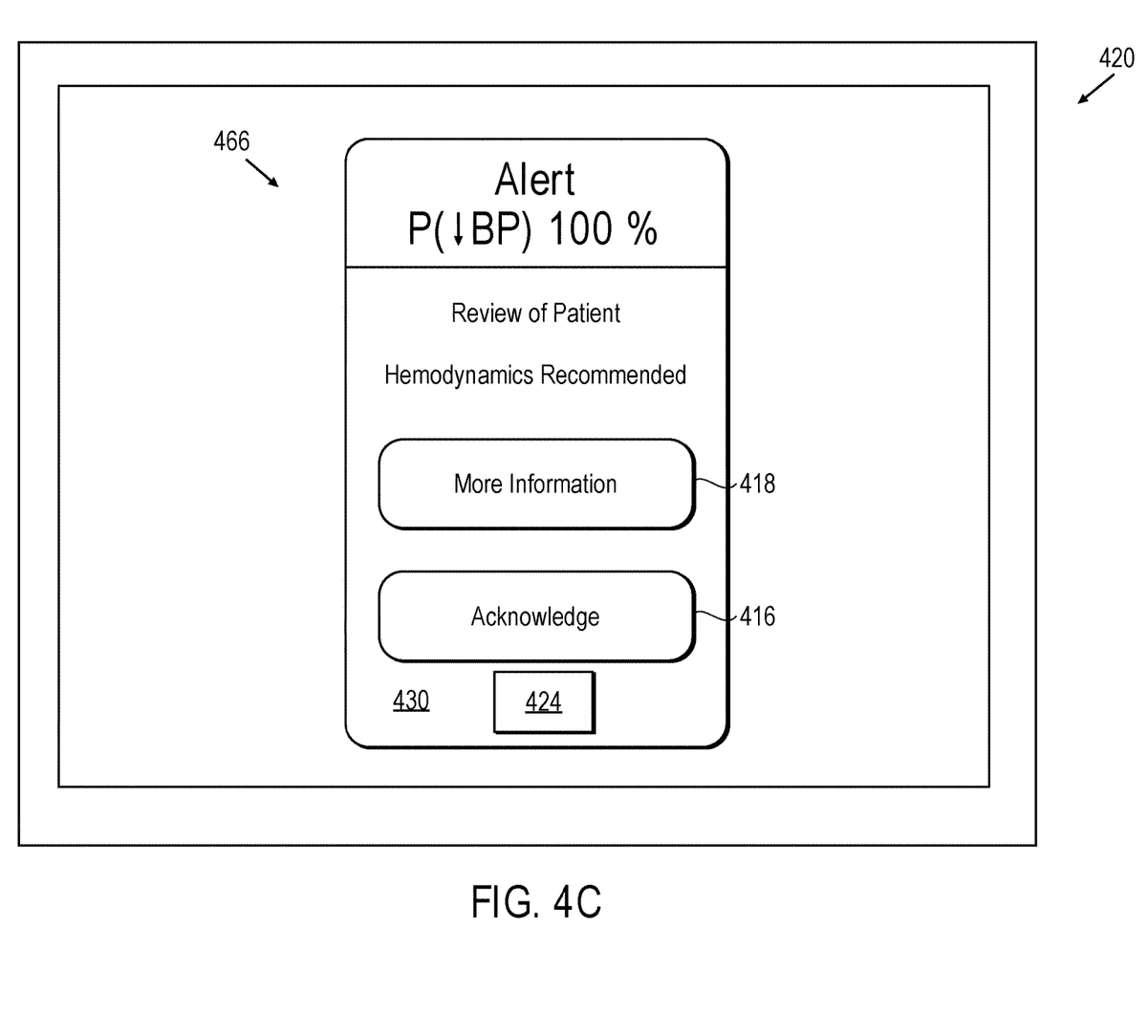
FIG. 4C shows an exemplary alarm screen of a hypotension predictive GUI overlaid as a pop-up on a display of a health monitoring unit, according to one implementation.

Referring to FIG. 4C in combination with FIGS. 1, 2A, and 3, flowchart 360 continues with overlaying alarm screen 466 as a pop-up on display 120/420 of health monitoring unit 102 if P($\downarrow$BP) 484 of living subject 140 satisfies a predetermined risk criteria (action 366). Overlay of alarm screen 466 on display 120/420 of health monitoring unit 102 is performed by hypotension predictive GUI 130/230/430, executed by system processor 104, and through use of overlay module 236.

The predetermined risk criteria may be based on the value of P($\downarrow$BP) 484, on the trend of P($\downarrow$BP) 484 over a time interval, or both. For example, having P($\downarrow$BP) 484 exceed a threshold of 85, for instance, may cause alarm screen 466 to pop-up substantially immediately. Alternatively, or in addition, a lower risk score may cause alarm screen 466 to pop-up if it exceeds a predetermined threshold over the entirety of a predetermined time period.

Thus, for example, while having P($\downarrow$BP) 484 equal to 85 or more may cause alarm screen 466 to pop-up substantially immediately, having P($\downarrow$BP) 484 at or above 80 may cause alarm screen 466 to pop-up after several seconds at that level, such as ten to thirty seconds in which P($\downarrow$BP) 484 is continuously between 80 and 85, for example. By analogy, a still lower value of P($\downarrow$BP) 484 may cause alarm screen 466 to pop-up if that P($\downarrow$BP) value is maintained continuously for one or more minutes. In yet another implementation, P($\downarrow$BP) 484 may cause alarm screen 466 to pop-up if it meets or exceeds a predetermined value a predetermined number of times over a predetermined time period. For example, having P($\downarrow$BP) 484 exceed 75 three times over a five minute interval may cause alarm screen 466 to pop-up.

Once alarm screen 466 does pop-up, alarm screen 466 overlays display 120/420 persistently until an acknowledgement input is received from user 146 via hypotension predictive GUI 130/230/430. For example, user 146 may either simply acknowledge the alarm by selecting acknowledge bar 416, or may request more information by selecting more information bar 418. Selection of acknowledge bar 416 by user 146 may cause alarm screen 466 to disappear, while selection of more information bar 418 may provide user 146 with direct access to the HPI diagnostic screen, described below, which includes additional data for evaluating the probability and likely cause of a future hypotension event for living subject 140. Thus, it is noted that the HPI diagnostic screen described below is accessible to user 146 from main screen 464 via shortcut button 490, as well as from alarm screen 466 via more information bar 418.

In some implementations, overlaying alarm screen 466 as a pop-up on display 120/420 causes sensory alarm 124/424 to be invoked. As noted above by reference to FIG. 1, sensory alarm 124/424 may be implemented as one or more of a visual alarm, an audible alarm, and a haptic alarm. For example, when implemented to provide a visual alarm, sensory alarm 124/424 may be invoked as flashing and/or colored graphics shown by hypotension predictive GUI 130/230/430 on display 120/420, and/or may include displaying P($\downarrow$BP) 484 via hypotension predictive GUI 130/230/430 on display 120/420. When implemented to provide an audible alarm, sensory alarm 124/424 may be invoked as any suitable warning sound, such as a siren or repeated tone. Moreover, when implemented to provide a haptic alarm, sensory alarm 124/424 may cause health monitoring unit 102 to vibrate or otherwise deliver a physical impulse perceptible to user 146.

Figure 4D:
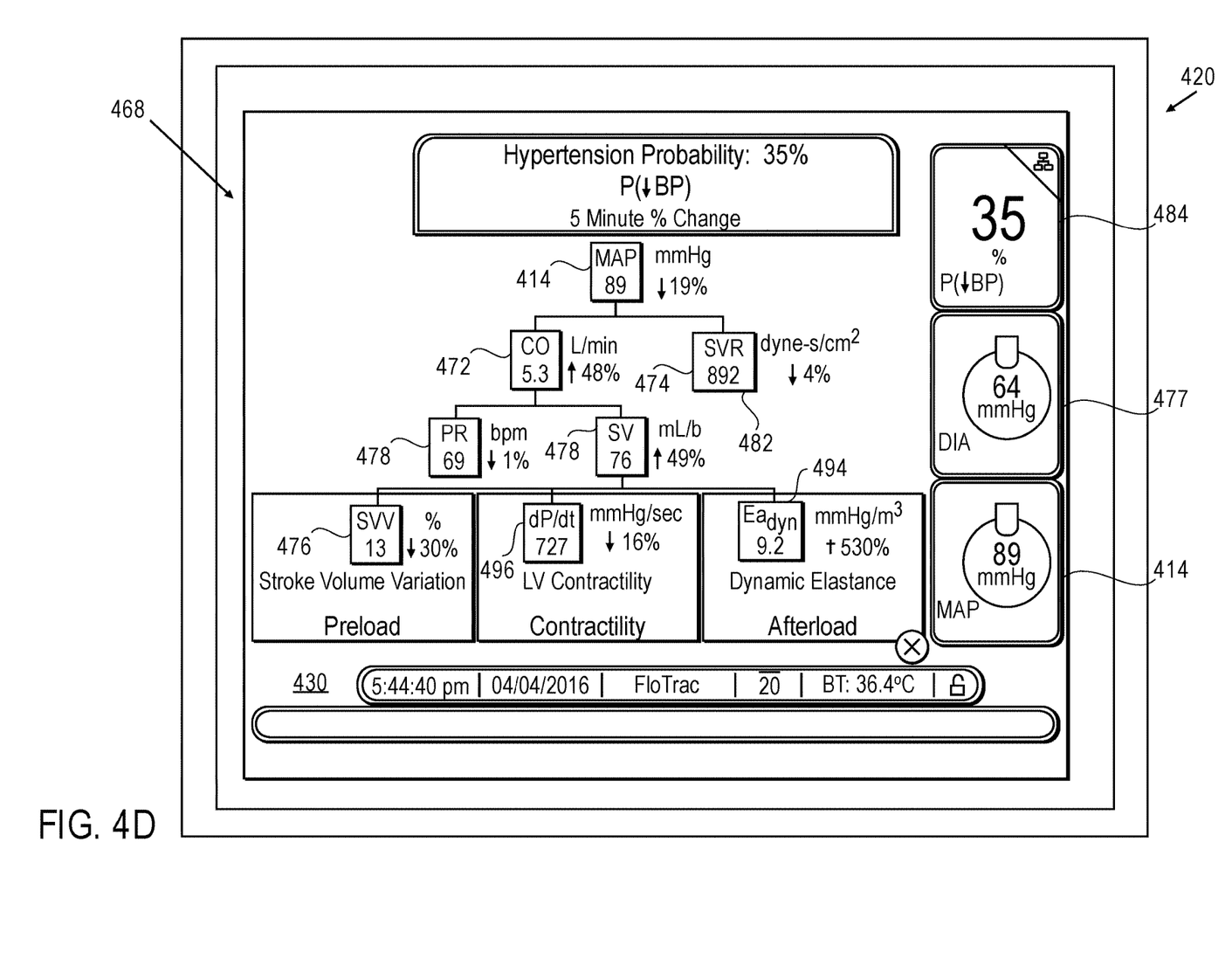
FIG. 4D shows an exemplary hypotension probability index (HPI) diagnostic screen of a hypotension predictive GUI provided on a display of a health monitoring unit, according to one implementation.

Referring to FIG. 4D in combination with FIGS. 1, 2A, and 3, flowchart 360 can conclude with enabling user 146 to access HPI diagnostic screen 468 showing a subset of health parameters 112/412 identified as hypotension risk indicators predictive of a future hypotension event for living subject 140 (action 368). Access to HPI diagnostic screen 468 is enabled by hypotension predictive GUI 130/230/430, executed by system processor 104, and through use of user access module 238.

As shown in FIG. 4D, in addition to the numerical values for CO 472 and P($\downarrow$BP) 484 shown on main screen 464 of hypotension predictive GUI 130/230/430, HPI diagnostic screen 468 of hypotension predictive GUI 130/230/430 shows numerical values and variations for hypotension risk indicators identified as predictive of a future hypotension event. According to the exemplary implementation shown by FIG. 4D, the hypotension risk indicators include MAP

114/414, DIA 477, SVR 482, SV 474, PR 478, SVV 476, arterial elastance ($E_a$) 494, and left ventricle contractility (dP/dt) 496.

The hypotension risk indicators shown as predictive health parameters on HPI diagnostic screen 468 can enable user 146 to identify a most probable cause of the future hypotension event for living subject 140. For example, HPI diagnostic screen 468 provided by hypotension predictive GUI 130/230/430 may enable user 146 to identify one or more of poor vascular tone, low blood volume, or reduced cardiac contractility, to name a few exemplary causes, as a most probable cause of a predicted future hypotension event.

Furthermore, in some implementations, the predictive health parameters shown on HPI diagnostic screen 468 can enable user 146 to determine a medical intervention for preventing the future hypotension event for living subject 140. For example, values and variations for MAP 414, CO 472, SVV 476, and SV 474 are highlighted in green on HPI diagnostic screen 468, indicating that those health parameters are low risk with respect to the probability of a hypotension event for living subject 140. Values and variations for PR 478 and SVR 482 are highlighted in yellow on HPI diagnostic screen 468, indicating that those health parameters are moderate risk with respect to the probability of a hypotension event for living subject 140.

It is noted that the predictive health parameters shown on HPI diagnostic screen 468 are drawn on HPI diagnostic screen 468 as a tree with MAP 414 at the top, and CO 472 and SVR 482 being linked to one another below MAP 414 by a branched connection coming from MAP 414. PR 478 and SV 474 are similarly linked to one another below CO 472 by a branched connection coming from CO 472. In addition, SVV 476, dP/dt 496, and $E_a$ 494 are linked to one another below SV 474 by a branched connection coming from SV 474. Based on the information shown by HPI diagnostic screen 468, i.e., P(↓BP) 484 at a relatively safe level of 35, a hypotension event is not imminent for living subject 140.

Moving to FIGS. 5A and 5B, FIGS. 5A and 5B show an implementation of hypotension predictive GUI 130/230/530 in which the main screen of hypotension predictive GUI 130/230/530 displays health parameters 112 using a speedometer type display format. As shown by FIG. 5A, selection screen 562 of hypotension predictive GUI 130/230/530 enables user 146 to select from among the same health parameters 112/412 shown in FIG. 4A, i.e., CO 572, SV 574, SVV 576, DIA 577, PR 578, SVI 580, SVR 582, MAP 514, and HPI 584, as well as SVRI, CI, and SYS. Thus health parameters 512 correspond respectively to health parameters 112/412 and may share any of the characteristics attributed to those corresponding features above. Also shown in FIG. 5A is exit button 586 enabling user 546 to close selection screen 562 of hypotension predictive GUI 130/230/530.

According to the exemplary implementation shown by FIG. 5A, hypotension predictive GUI 130/230/530 is implemented as a touch screen user interface. However, in other implementations, hypotension predictive GUI 130/230/530 may be configured to receive inputs 128 from user 146 via a keyboard, via another type of input device, such as a mouse or pressure pad, or as voice commands spoken by user 146, for example. As shown by the shadowing of parameters 576, 578, and 580, user 146 has selected SVV 576, MAP 514, and HPI 584 for viewing on display 120/520 of health monitoring unit 102 from among health parameters 112/412/512 being tracked by health monitoring unit 102.

Referring to FIG. 5B, FIG. 5B shows main screen 564 of hypotension predictive GUI 130/230/530 displaying parameters SVV 576, MAP 514, and P(↓BP) 584 selected by user 146 from selection screen 562. As shown by FIG. 5B, main screen 564 of hypotension predictive GUI 130/230/430/530 also provides shortcut button 590 enabling user 146 direct access to an HPI diagnostic screen corresponding to HP diagnostic screen 468, in FIG. 4D, and including additional data for evaluating the probability and likely cause of a future hypotension event for living subject 140.

As further shown by FIG. 5B, the health parameters shown on main screen 564 of hypotension predictive GUI 130/230/530 are displayed by reference to color coded risk zones. For example, in the value reported for P(↓BP) 584 is shown to fall in a relatively safe green zone. The value for MAP 514 is shown to fall in a yellow zone, indicating that the value of MAP 514 presents moderate risk with respect to the probability of a hypotension event for living subject 140. By contrast to health parameters highlighted in green or yellow, the value of SVV 576 is shown to have increased into a red zone, indicating that SVV 25 is a high risk health parameter with respect to the probability of a hypotension event for living subject 140.

In the event that P(↓BP) 584 or one or more others of health parameters 112/412/512 satisfies a predetermined risk criteria, as described above by reference to FIG. 4C, alarm screen 466 may overlay 120/420/520 as a pop-up. Overlay of alarm screen 466 on display 120/420/520 of health monitoring unit 102 is performed by hypotension predictive GUI 130/230/430, executed by system processor 104, and through use of overlay module 236.

As discussed above, once alarm screen 466 does pop-up, alarm screen 466 overlays display 120/420/520 persistently until an acknowledgement input is received from user 146 via hypotension predictive GUI 130/230/430/530. For example, user 146 may either simply acknowledge the alarm by selecting acknowledge bar 416, or may request more information by selecting more information bar 418. Selection of acknowledge bar 416 by user 146 may cause alarm screen 466 to disappear, while selection of more information bar 418 may provide user 146 with direct access to HPI diagnostic screen 468, described above.

Thus, the hypotension predictive GUI of the health monitoring unit disclosed by the present application provides a user with powerful options for monitoring and evaluating the probability of a future hypotension event for a living subject. By providing a selection screen on a display of the health monitoring unit, the hypotension predictive GUI disclosed by the present application enables the user to select parameters for viewing on the display from among the health parameters of the living subject being tracked by the health monitoring unit. By presenting a main screen on the display that includes an icon for communicating the HPI status of the living subject regardless of the parameters selected by the user, the hypotension predictive GUI disclosed by the present application renders the HPI status of the living subject continuously observable by the user.

In addition, by overlaying an alarm screen as a pop-up on the health monitoring unit display if the HPI of the living subject satisfies a predetermined risk criteria, the hypotension predictive GUI disclosed by the present application ensures that a timely warning of a future hypotension event is provided to the user. Moreover, by enabling the user to access an HPI diagnostic screen showing values for a subset of the health parameters identified as predictive of the future hypotension event, the hypotension predictive GUI disclosed by the present application provides detailed diagnostic information allowing the user to identify a most probable cause of the future hypotension event as well as possible medical interventions for its prevention.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

What is claimed is:

1. A system for monitoring of arterial pressure of a patient and providing a warning to medical personnel of a predicted future hypotension event, the system comprising:
    a hemodynamic sensor that produces an analog hemodynamic sensor signal representative of an arterial pressure waveform of the patient;
    an analog-to-digital converter that converts the analog hemodynamic sensor signal to digital hemodynamic data;
    a system memory that stores hypotension prediction software code and a graphical user interface;
    a display; and
    a hardware processor that is configured to:
        execute the hypotension prediction software code to:
            derive, from the digital hemodynamic data, a plurality of health parameters; and
            determine a hypotension probability index (HPI) representing a probability of a future hypotension event for the patient based on the plurality of health parameters, and execute the graphical user interface to:
        provide a selection screen on the display enabling a user to select a plurality of parameters for viewing on the display from among health parameters of the patient being tracked by the system and being stored in the system memory;
        overlay an alarm screen as a pop-up on the display in response to the HPI of the patient satisfying a predetermined risk criterion; and
        provide an HPI diagnostic screen showing values for one or more of the plurality of health parameters.

2. The health monitoring unit of claim 1, wherein the hardware processor causes the alarm screen to be persistently displayed until an input is received from the user via the graphical user interface.

3. The health monitoring unit of claim 1, wherein the main screen shows the HPI as a function of time.

4. The health monitoring unit of claim 1, wherein the graphical user interface displays graphical control elements that enable the user to access the HPI diagnostic screen from the main screen and the alarm screen.

5. The health monitoring unit of claim 1, wherein the HPI diagnostic screen displays predictive health parameters to assist the user in identifying a most probable cause of the future hypotension event.

6. The health monitoring unit of claim 1, wherein the HPI diagnostic screen displays predictive health parameters to assist the user in determining a medical intervention for preventing the future hypotension event.

7. The health monitoring unit of claim 1, wherein a plurality of predicative health parameters including mean arterial pressure (MAP), cardiac output (CO), systemic vascular resistance (SVR), pulse rate (PR), stroke volume (SV), stroke volume variation (SVV), left ventricle contractility (dP/dt), and arterial elastance ($E_a$) are drawn on the HPI diagnostic screen as a tree with MAP at the top, with CO and SVR linked to one another below MAP by a branched connection coming from MAP, with PR and SV linked to one another below CO by a branched connection coming from CO, and with SVV, dP/dt, and $E_a$ linked to one another below SV by a branched connection coming from SV.

8. The system of claim 1, wherein the graphical user interface includes a selection module that provides the selection screen on the display, a presentation module that presents the main screen on the display, an overlay module that overlays the alarm screen as a pop-up on the display, and a user access module that provides the HPI diagnostic screen on the display.

9. The system of claim 1, wherein the display comprises a touch screen user interface.

10. The system of claim 1, wherein the plurality of parameters presented by the selection screen include cardiac output, stroke volume, stroke volume variation, diastolic pressure, pulse rate, stroke volume index, systemic vascular resistance, mean arterial pressure, and hypotension probability index.

11. The system of claim 10, wherein the plurality of parameters presented by the selection screen further include systemic vascular resistance index, cardiac index, and systolic pressure.

12. The system of claim 1, wherein the main screen includes a numerical representation of the HPI.

13. The system of claim 12, wherein the numerical representation of the HPI is a number between zero and one hundred.

14. The system of claim 1, wherein the alarm screen includes a numerical representation of the HPI.

15. The system of claim 1, wherein the HPI diagnostic screen includes a numerical representation of the HPI.

16. The system of claim 1, wherein once the alarm screen is overlaid as a pop-up on the display, the alarm screen overlays the display persistently until an acknowledgement input is provided via the graphical user interface.

17. The system of claim 16, wherein the alarm screen includes an acknowledgement bar that is selectable to produce the acknowledgement input.

18. The system of claim 17, wherein the alarm screen includes an information bar that is selectable to allow access to the HPI diagnostic screen.

19. The system of claim 1, wherein the HPI diagnostic screen is accessible from the main screen via a shortcut button.

20. The system of claim 1, wherein overlaying the alarm screen as a pop-up causes a sensory alarm to be invoked by the hardware processor.

21. The system of claim 20, wherein the sensory alarm is a visual alarm that is invoked as flashing or colored graphics shown by the graphical user interface on the display.

22. The system of claim 20, wherein the sensory alarm is an audible alarm.

23. The system of claim 20, wherein the sensor alarm is a haptic alarm.

24. The system of claim 1, wherein the hardware processor is configured to cause the alarm screen to pop-up immediately when the HPI satisfies a first risk criterion.

25. The system of claim 24, wherein the hardware processor is configured to cause the alarm screen to pop-up when the HPI satisfies a second risk criterion continuously for a first predetermined time period.

26. The system of claim 25, wherein the hardware processor is configured to cause the alarm screen to pop-up when the HPI satisfies a third risk criterion continuously for a second, longer, predetermined time period.

27. The system of claim 24, wherein the hardware processor is configured to cause the alarm screen to pop-up when the HPI satisfies a fourth risk criterion a predetermined number of times over a predetermined time interval.

* * * * *